US011022602B2

(12) United States Patent
Carlson et al.

(10) Patent No.: US 11,022,602 B2
(45) Date of Patent: Jun. 1, 2021

(54) ANTIBIOTIC-BASED CONJUGATES AND METHODS OF USE THEREOF

(71) Applicant: REGENTS OF THE UNIVERSITY OF MINNESOTA, Minneapolis, MN (US)

(72) Inventors: Erin Elizabeth Carlson, Minneapolis, MN (US); Shabnam Sharifzadeh, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

(21) Appl. No.: 15/947,302

(22) Filed: Apr. 6, 2018

(65) Prior Publication Data
US 2018/0292387 A1  Oct. 11, 2018

Related U.S. Application Data

(60) Provisional application No. 62/484,318, filed on Apr. 11, 2017.

(51) Int. Cl.
| | |
|---|---|
| *C07D 477/00* | (2006.01) |
| *C07D 501/20* | (2006.01) |
| *G01N 33/50* | (2006.01) |
| *A61K 47/55* | (2017.01) |
| *A61K 47/22* | (2006.01) |
| *A61P 31/04* | (2006.01) |
| *A61K 31/397* | (2006.01) |
| *A61K 49/00* | (2006.01) |
| *G01N 33/58* | (2006.01) |
| *G01N 33/566* | (2006.01) |
| *G01N 33/532* | (2006.01) |
| *A61K 47/12* | (2006.01) |
| *A61K 47/16* | (2006.01) |

(52) U.S. Cl.
CPC ....... *G01N 33/5008* (2013.01); *A61K 31/397* (2013.01); *A61K 47/22* (2013.01); *A61K 47/552* (2017.08); *A61K 49/0021* (2013.01); *A61K 49/0041* (2013.01); *A61K 49/0052* (2013.01); *A61P 31/04* (2018.01); *C07D 477/00* (2013.01); *C07D 501/20* (2013.01); *G01N 33/532* (2013.01); *G01N 33/566* (2013.01); *G01N 33/58* (2013.01); *A61K 47/12* (2013.01); *A61K 47/16* (2013.01)

(58) Field of Classification Search
CPC .......................... C07D 477/00; C07D 501/20
See application file for complete search history.

(56) References Cited

U.S. PATENT DOCUMENTS

| | | | |
|---|---|---|---|
| 9,521,845 | B2 | 12/2016 | Sieber et al. |
| 2014/0193831 | A1 | 7/2014 | Van Der Hoorn et al. |
| 2016/0221977 | A1 | 8/2016 | Sello et al. |
| 2018/0339972 | A1 | 11/2018 | Carlson et al. |

FOREIGN PATENT DOCUMENTS

WO  2016069542 A2  5/2016

OTHER PUBLICATIONS

CAPLUS data base and Registry No. 1064579-42-5, 2008.*
Registry No. 851509-18-7, 2005 CAPLUS.*
Watanabe et al. Chem. Eur. J. 2011, 17, 8342-8349.*
RN 1064579-42-5 Registry in STNext, 2008.*
U.S. Appl. No. 15/988,986, 2018-0339972.
Blumberg, et al., "Isolation by Covalent Affinity Chromatography of the Penicillin-Binding Components from Membranes of Bacillus subtilis", Proc Natl Acad Sci U S A 69, 3751-3755 (1972).
Bottcher, et al., "β-Lactams and β-lactones as activity-based probes in chemical biology", Med. Chem. Commun. 3, 408-417 (2012).
Clatworthy, et al., "Targeting virulence: a new paradigm for antimicrobial therapy", Nat Chem Biol 3, 541-548 (2007).
Daniel, et al., "Control of cell morphogenesis in bacteria: two distinct ways to make a rod-shaped cell", Cell 113, 767-776 (2003).
Falconer, et al., "Antibiotics as probes of biological complexity", Nat. Chem. Biol. 7, 415-423 (2011).
Fisher, et al., "Bacterial resistance to beta-lactam antibiotics: compelling opportunism, compelling opportunity", Chem. Rev. 105, 395-424 (2005).
Foss, et al., "Chemical—Biological Studies of Subcellular Organization in Bacteria", Biochemistry 50, 7719-7734 (2011).
Kocaoglu, et al., "Activity-Based Probes for Selective Penicillin-Binding Protein Visualization", Bioorganic Gordon Research Conference, Andover, NH, Jun. 5-10, 2016.
Kocaoglu, et al., "Profiling of β-Lactam Selectivity for Penicillin-Binding Proteins in *Escherichia coli* Strain DC2", Antimicrob. Agents Chemother. 59, 2785-2790 (2015).
Kocaoglu, et al., "Profiling of β-Lactam Selectivity for Penicillin-Binding Proteins in *Streptococcus pneumoniae* D39", Antimicrob. Agents Chemother. 59, 3548-3555 (2015).

(Continued)

*Primary Examiner* — Brian E McDowell

(74) *Attorney, Agent, or Firm* — Viksnins Harris Padys Malen LLP

(57) ABSTRACT

The invention provides a conjugate of formula I:

R-L-Y                                    I or a salt thereof, wherein R, L, and Y have any of the values described in the specification, as well as compositions comprising a conjugate of formula I. The conjugates are useful for labeling.

2 Claims, 3 Drawing Sheets

(56) References Cited

OTHER PUBLICATIONS

Kocaoglu, et al., "Progress and prospects for small-molecule probes of bacterial imaging", Nat. Chem. Bio. 12, 472-478 (2016).
Kocaoglu, et al., "Selective Penicillin-Binding Protein Imaging Probes Reveal Substructure in Bacterial Cell Division", ACS Chem Biol 7, 1746-1753 (2012).
Lakaye, et al., "Synthesis, purification and kinetic properties of fluorescein-labelled penicillins", Biochem. J. 300 (Pt 1), 141-145 (1994).
Liu, et al., "Activity-based protein profiling: the serine hydrolases", Proc Natl Acad Sci U S A 96, 14694-14699 (1999).
McPherson, et al., "Two Class A High-Molecular-Weight Penicillin-Binding Proteins of Bacillus subtilis Play Redundant Roles in Sporulation", J. Bacteriol. 183, 6046-6053 (2001).
Rowley, et al., "The site of action of penicillin. 1. Uptake of penicillin on bacteria", Biochem J 46, 157-161 (1950).
Sauvage, et al., "The penicillin-binding proteins: structure and role in peptidoglycan biosynthesis", Ferns Microbiol Rev 32, 234-258 (2008).
Scheffers, et al., "Several distinct localization patterns for penicillin-binding proteins in Bacillus subtilis", Mol Microbiol 51, 749-764 (2004).
Sharifzadefi, et al., "Activity-Based Probes for Selective Penicillin-Binding Protein Visualization", International Chemical Biology Symposium, Madison, WI, Oct. 24-26, 2016.
Speers, et al., "Profiling enzyme activities in vivo using click chemistry methods", Chem Biol 11, 535-546 (2004).
Spratt, et al., "Penicillin-binding proteins and cell shape in *E. coli*", Nature 254, 516-517 (1975).
Staub, et al., "β-Lactams as Selective Chemical Probes for the in Vivo Labeling of Bacterial Enzymes Involved in Cell Wall Biosynthesis, Antibiotic Resistance, and Virulence", J Am Chem Soc 130, 13400-13409 (2008).
Tiyanont, et al., "Imaging peptidoglycan biosynthesis in Bacillus subtilis with fluorescent antibiotics", Proc Natl Acad Sci U S A 103, 11033-11038 (2006).
Tsien, "The green fluorescent protein", Annu Rev Biochem 67, 509-544 (1998).
Vollmer, et al., "Peptidoglycan structure and architecture", FEMS Microbiol Rev 32, 149-167 (2008).
Zhao, et al., "Bocillin FL, a sensitive and commercially available reagent for detection of penicillin-binding proteins", Antimicrob Agents Chemother 43, 1124-1128 (1999).
Garner, et al., "Immunomodulation and the quorum sensing molecule 3-oxo-C12-homoserine lactone: the importance of chemical scaffolding for probe development", Chem Commun 49, 1515-1517 (2013).
Indiana University, Calendar announcement of Ph.D. Defense of Ozden Kocaoglu on Tuesday, Dec. 9, 2014, Downloaded on Jan. 18, 2019 from http://onestart.iu.edu/ccl-prd/EventMaintenance.do?methodtocall=viewEvent&eventil=10951377&pubcalld=GRP1342 (2014).
Indiana University, The University Graduate School, thesis guidelines, downloaded on Jan. 21, 2019 from: https://graduate.indiana.edu/thesis-dissertation/submission/doctoral.html (2019).
Kocaoglu, "Activity-based probes for selective penicillin-binding protein visualization", PhD Thesis Indiana University, UMI No. 3669379, Published by ProQuest LLC, 240 pages (2014).
Pu, et al., "Synthesis and acylation of salts of L-threonine .beta.-lactone: a route to .beta.-lactone antibiotics", J Org Chem 59, 3642-3655 (1994).
Aldridge, et al., "Antibiotic 1233A: a fungal-lactone", J Chem Soc Perkin 1, 23, 3888-3891 (1971).
Bisson-Filho, et al., "Treadmilling by FtsZ filaments drives peptidoglycan synthesis and bacterial cell division", Science 355, 739-743 (2017).
Boersma, et al., "Minimal Peptidoglycan (PG) Turnover in Wild-Type and PG Hydrolase and Cell Division Mutants of *Streptococcus pneumoniae* D39 Growing Planktonically and in Host-Relevant Biofilms", J Bacteriol 197, 3472-3485 (2015).
Bottcher, et al., "β-Lactones as Privileged Structures for the Active-Site Labeling of Versatile Bacterial Enzyme Classes", Angew Chem Int Ed 47, 4600-4603 (2008).
Bottcher, et al., "β-Lactones as Specific Inhibitors of ClpP Attenuate the Production of Extracellular Virulence Factors of *Staphylococcus aureus*", J Am Chem Soc 130, 14400-14401 (2008).
Bush, et al., "Improved sensitivity in assays for binding of novel beta-lactam antibiotics to penicillin-binding proteins of *Escherichia coli*", Antimicrobial Agents Chemother 31(8), 1271-1273 (1987).
Carlson, "Imaging of Penicillin-Binding Protein Activity in *Streptococcus pneumoniae*", Presentation at American Chemical Society, 21 pages, Mar. 28, 2017.
Compton, et al., "Antibacterial Activity of and Resistance to Small Molecule Inhibitors of the ClpP Peptidase", ACS Chem Biol 8(12), 2669-2677 (2013).
Dargis, et al., "Use of Biotinylated r-Lactams and Chemiluminescence for Study and Purification of Penicillin-Binding Proteins in Bacteria", Antimicrob Agents Ch 8, 973-980 (1994).
Dominguez-Escobar, et al., "Processive movement of MreB-associated cell wall biosynthetic complexes in bacteria", Science 333, 225-228 (2011).
Fleurie, et al., "Interplay of the Serine/Threonine-Kinase StkP and the Paralogs DivIVA and GpsB in Pneumococcal Cell Elongation and Division", PloS Genet 10(4), e1004275, 18 pages (2014).
Garner, et al., "Coupled, circumferential motions of the cell wall synthesis machinery and MreB filaments in B. subtilis", Science 333, 222-225 (2011).
Goffin, et al., "Biochemistry and Comparative Genomics of SxxK Superfamily Acyltransferases Offer a Clue to the Mycobacterial Paradox: Presence of Penicillin-Susceptible Target Proteins versus Lack of Efficiency of Penicillin as Therapeutic Agent", Microb Mol Biol Rev 66, 702-738 (2002).
Gordon, et al., "The crystal structure of the penicillin-binding protein 2x from *Streptococcus pneumoniae* and its acyl-enzyme form: implication in drug resistance", J Mol Biol 299, 477-485 (2000).
Hakenbeck, et al., "Molecular mechanisms of β-lactam resistance in *Streptococcus pneumoniae*", Future Microbiol 7, 395-410 (2012).
Kim, et al., "Cleavage of beta-lactone ring by serine protease. Mechanistic implications", Bioorg Med Chem 10, 2553-2560 (2002).
Kocaoglu, "Activity-Based Probes for Selective Penicillin-Binding Protein Visualization", Thesis submitted in partial fullfilment of the requirements for degree, Doctor of Philosophy in the Dept. of Molecular and Cellular Biochemistry Indiana University, Dec. 2014, 239 pages (sequestered through Dec. 22, 2016.).
Krysiak, et al., "Quantitative Map of β-Lactone-Induced Virulence Regulation", J Proteome Res 16(3), 1180-1192 (2017).
Kuru, et al., "In Situ probing of newly synthesized peptidoglycan in live bacteria with fluorescent D-amino acids", Angew Chem Int Ed Engl 51, 12519-12523 (2012).
Land, et al., "Requirement of Essential Pbp2x and GpsB for Septal Ring Closure in *Streptococcus pneumoniae* D39", Mol Microbiol 90, 939-955 (2013).
Landgraf, et al., "Segregation of molecules at cell division reveals native protein localization", Nat Methods 9, 480-482 (2012).
Lebar, et al., "Reconstitution of Peptidoglycan Cross-Linking Leads to Improved Fluorescent Probes of Cell Wall Synthesis", J Am Chem Soc 136, 10874-10877 (2014).
Li, et al., "Scaling Proteome-Wide Reactions of Activity-Based Probes", Anal Chem 89, 6295-6299 (2017).
Liechti, et al., "A new metabolic cell-wall labelling method reveals peptidoglycan in Chlamydia trachomatis", Nature 506, 507-510 (2014).
Macheboeuf, et al., "Penicillin binding proteins: key players in bacterial cell cycle and drug resistance processes", FEMS Microbiol Rev 30, 673-691 (2006).
Margolin, et al., "The Price of Tags in Protein Localization Studies", J Bacteriol 194, 6369-6371 (2012).
Massidda, et al., "From models to pathogens: how much have we learned about *Streptococcus pneumoniae* cell division?", Environ Microbiol 15, 3133-3157 (2013).

(56) References Cited

OTHER PUBLICATIONS

Oh, et al., "Potential pharmacological chaperones targeting cancer-associated MCL-1 and Parkinson disease-associated α-synuclein", PNAS 111(30), 11007-11012 (2014).
Parker, et al., "SQ 26,517—A beta-Lactone Produced by a Bacillus Species", J Antibiot 35, 900-902 (1982).
Pidgeon, et al., "Metabolic Profiling of Bacteria by Unnatural C-terminated D-Amino Acids", Angew Chem Int Ed Engl 54, 6158-6162 (2015).
Rued, et al., "Suppression and Synthetic-Lethal Genetic Relationships of ΔgpsB Mutations Indicate That GpsB Mediates Protein Phosphorylation and Penicillin-Binding Protein Interactions in *Streptococcus pneumoniae* D39", Mol Microbiol 103, 931-97 (2017).
Sauvage, et al., "The penicillin-binding proteins: structure and role in peptidoglycan biosynthesis", FEMS Microbiology Reviews 32(3), 556 (2008).
Sharifzadeh, et al., "Novel Electrophilic Scaffold for Imaging of Essential Penicillin-Binding Proteins in *Streptococcus pneumoniae*", ACS Chem Biol 12(11), 2849-2857 (2017).
Sharifzadeh, et al., "Profiling of β-Lactam Selectivity for Penicillin-Binding Proteins in Bacillus subtilis and Methicillin- Sensitive and -Resistant *Staphylococcus aureus*", Poster, Chemical Biology Training Grant Symposium, 7 pages, May 25, 2016.
Sharifzadeh, et al., "Visualization of Penicillin-Binding Proteins in *Streptococcus pneumoniae* Using a Variety of Activity-Based Probes", Poster, MIKI Conference, 7 pages, Apr. 8, 2017.
Shieh, et al., "Imaging bacterial peptidoglycan with near-infrared fluorogenic azide probes", Proc Natl Acad Sci 111, 5456-5461 (2014).
Siegrist, et al., "(D)-Amino acid chemical reporters reveal peptidoglycan dynamics of an intracellular pathogen", ACS Chem Biol 8, 500-503 (2013).
Swulius, et al., "The Helical MreB Cytoskeleton in *Escherichia coli* MC1000/pLE7 Is an Artifact of the N-Terminal Yellow Fluorescent Protein Tag", J Bacteriol 194(23), 6382-6386 (2012).
Tsui, et al., "Pbp2x localizes separately from Pbp2b and other peptidoglycan synthesis proteins during later stages of cell division of *Streptococcus pneumoniae* D39", Mol Microbiol 94, 21-40 (2014).
Tymiak, et al., "Structure of obafluorin: an antibacterial .beta.-lactone from Pseudomonas fluorescens", J Org Chem 50(26), 5491-5495 (1985).
Venukadasula, et al., "A Concise, Phosphate-Mediated Approach to the Total Synthesis of (-)-Tetrahydrolipstatin", Org Lett 12, 1556-1559 (2010).
Wang, et al., "beta-Lactone probes identify a papain-like peptide ligase in *Arabidopsis thaliana*", Nature Chemical Biology 4(9), 557-563 (2008). [Supplementay Information 15 pages].
Waxman, et al., "Penicillin-binding proteins and the mechanism of action of beta-lactam antibiotics", Annu Rev Biochem 52, 825-869 (1983).
Wells, et al., "Distribution of β-Lactam and β-Lactone Producing Bacteria in Nature", J Antibiot (Tokyo) 35, 814-821 (1982).
Wells, et al., "Obafluorin, a novel beta-lactone produced by Pseudomonas fluorescens. Taxonomy, fermentation and biological properties", J Antibiot (Tokyo) 37, 802-803 (1984).
Zeiler, et al., "Vibralactone as a Tool to Study the Activity and Structure of the ClpP1P2 Complex from Listeria monocytogenes", Angew Chem Int Ed Engl 50, 11001-11004 (2011).
Zhao, et al., "Mechanistic analysis of aliphatic β-lactones in Vibrio harveyi reveals a quorum sensing independent mode of action", Chem Commun 52, 11971-11974 (2016).

\* cited by examiner

* protein concentrations adjusted at 5mg/ml

ANTIBIOTIC-BASED CONJUGATES AND METHODS OF USE THEREOF

PRIORITY

This application claims priority to U.S. Provisional Patent Application No. 62/484,318, filed 11 Apr. 2017. The entire content of this United States Provisional Patent Application is hereby incorporated herein by reference.

GOVERNMENT FUNDING

This invention was made with government support under DP2OD008592-02 awarded by the National Institutes of Health. The government has certain rights in this invention.

BACKGROUND

Most bacteria are surrounded by a cell wall composed of a complex polymeric structure called peptidoglycan (PG) that is essential for cell survival (Vollmer, W., et al. FEMS Microbiol. Rev. 2008, 32, 149-167). The biosynthetic pathway for production of PG and the proteins required for its assembly have been the targets for many antibacterial agents (Sauvage, E., FEMS Microbiol. Rev. 2008, 32, 556-556). For example, penicillin-binding proteins (PBPs), which polymerize and crosslink strands of PG also have affinity for the β-lactam antibiotic penicillin (Rowley, D., et al. Biochem. J. 1950, 46, 57-161; and Blumberg, P. M., Proc. Natl. Acad. Sci. U.S.A. 1972, 69, 3751-3755). PBPs are classified into three groups based upon their molecular weight and conserved amino acid motifs: class A and class B high molecular weight (HMW) PBPs and low molecular weight (LMW) PBPs. Class A HMW PBPs have an N-terminal domain which possesses glycosyltransferase activity and a C-terminal domain that performs transpeptidation. Class B HMW PBPs have C-terminal transpeptidase activity and unknown N-terminal functions. LMW PBPs commonly have D,D-carboxypeptidase activity and play a major role in regulating cross-linking between glycan chains (McPherson, D. C., et al. J. Bacteriol. 2001, 183, 6046-6053). These proteins all contain a serine in their peptidase domain that is required for catalysis. Penicillin potentiates PBP function by forming a stable acyl-enzyme intermediate with this residue, which in turn inhibits crosslinking of PG. Despite the effectiveness of β-lactam antibiotics, bacterial resistance has arisen very rapidly (Clatworthy, A. E., et al. Nat. Chem. Biol. 2007, 3, 541-548; and Fisher, J. F., et al. Chem. Rev. 2005, 105, 395-424). A better and more detailed understanding of the mechanism of PG synthesis may be the key for design of new and more effective antibiotics.

Since the elucidation of penicillin's mechanism of action, it has been used as a probe to gain more insight into bacterial physiology (Falconer, S. B., et al. Nat. Chem. Biol. 2011, 7, 415-423; and Bottcher, T., et al. Med. Chem. Commun. 2012, 3, 408-417). A standard strategy for detection of PBP activity is tagging with a radiolabeled β-lactam, such as penicillin, and subsequent separation by sodium dodecyl sulfate-polyacrylamide gel electrophoresis (SDS-PAGE) and detection by fluorography (Spratt, B. G., et al. Nature 1975, 254, 516-517). Although this method is well established, radiolabeled β-lactam molecules are hazardous making them non-ideal to handle for routine or large-scale analysis. Furthermore, the experimental procedure is time consuming taking up to several days and most importantly, it cannot be used for in vivo visualization of PBPs. Fluorescent labeling has become a very useful tool for the monitoring of proteins in their native environment. Green fluorescent protein (GFP) is a well-known example that has been used to study protein expression and localization in living systems but requires genetic manipulation of each protein of interest and artificial fusions can disturb protein localization, function, and levels (Tsien, R. Y. Annu. Rev. Biochem. 1998, 67, 509-544; and Scheffers, D. J., et al. Mol. Microbiol. 2004, 51, 749-764). Fluorescently labeled small molecule probes can be used to overcome the disadvantages of both radioactivity- and protein fusion-based strategies with the additional benefit of directly detecting the activity state of the target (Kocaoglu, O., et al. Nat. Chem. Bio. 2016, 12, 472-478).

Small molecule-conjugated fluorophores that label their protein targets in an activity-dependent fashion can provide superior temporal resolution and their activity can be modulated by dose (Foss, M. H., et al. Biochemistry 2011, 50, 7719-7734). These compounds are also generally easy to use and enable visualization in a broad range of organisms. Fluorophore-conjugated vancomycin and ramoplanin have been generated and used to label PG biosynthetic precursors in various Gram-positive bacteria to reveal the sites of new PG synthesis in these organisms (Daniel, R. A., et al. Cell 2003, 113, 767-776; and Tiyanont, K., et al. Proc. Natl. Acad. Sci. U.S.A. 2006, 103, 11033-11038;). Besides radiolabeled penicillin, fluorophore-conjugated variants such as BOCILLIN-FL (Boc-FL), which is commercially available, have been developed to visualize bacterial PBPs (Lakaye, B., et al. Biochem. J. 1994, 300, 141-145; and Zhao, G., et al. Antimicrob. Agents Chemother. 1999, 43, 1124-1128) and peptidoglycan biosynthetic machinery in living cells. Although Boc-FL has been an important research tool, it visualizes all PBPs at once abrogating the possibility of exploring the function of only one or several PBPs. Accordingly, we sought to generate tools that would enable selective examination of a subset of PBPs in vivo.

It is anticipated that PBP selective probes could be obtained by derivatization of an antibiotic known to target only the desired PBPs. In 2008, Staub et al. synthesized a library of antibiotic-based chemical probes that included cephalosporin, aztreonam, and ampicillin analogs to tag catalytically active PBPs in *Pseudomonas putida, Listeria welshimeri,* and *Bacillus licheniformis*. Bacterial proteomes were labeled with these activity-based probes followed by attachment of a fluorophore tag (via click chemistry) and visualized using fluorescence gel scanning (Speers, A. E., et al. Chem. Biol. 2004, 11, 535-546; and Liu, Y., et al. Proc. Natl. Acad. Sci. U.S.A. 1999, 96, 14694-14699). Each compound labeled a different set of PBPs in the three organisms due to the structural differences between the three antibiotic-inspired probes (Staub, I., et al. J. Am. Chem. Soc. 2008, 130, 13400-13409).

Currently, there is a need for new agents that are useful for detecting PBPs.

SUMMARY

In one aspect the present invention provides conjugates having affinity for one or more PBPs that are useful for detecting PBPs in a cell or in a cell fraction comprising one or more PBPs.

Accordingly, the invention provides a conjugate of formula I:

or a salt thereof, wherein:
R is an antibiotic comprising a β-lactam;
L is a absent or a linking group; and
Y is azide, $(C_2-C_8)$alkynyl, 3-8 membered cycloalkyl comprising at least one triple bond, 1,2,4,5-tetrazinyl which is optionally substituted with $(C_1-C_8)$alkyl, a fluorescent group, or biotin;
provided that the conjugate is not

[chemical structure]

or a salt thereof; and
provided that R is not

[chemical structure]

or a salt thereof.

The invention also provides a composition comprising a compound of formula I or a salt thereof, and an excipient.

The invention also provides a pharmaceutical composition comprising a compound of formula I or a pharmaceutically acceptable salt thereof, and a pharmaceutically acceptable excipient.

The invention also provides a method for labeling one or more PBPs, contacting a cell or a cell fraction comprising one or more PBPs with a conjugate of formula I, or a salt thereof, wherein the conjugate binds to the one or more PBPs.

The invention also provides processes and intermediates disclosed herein that are useful for preparing a conjugate of formula I or a salt thereof.

DETAILED DESCRIPTION

Figure 1:
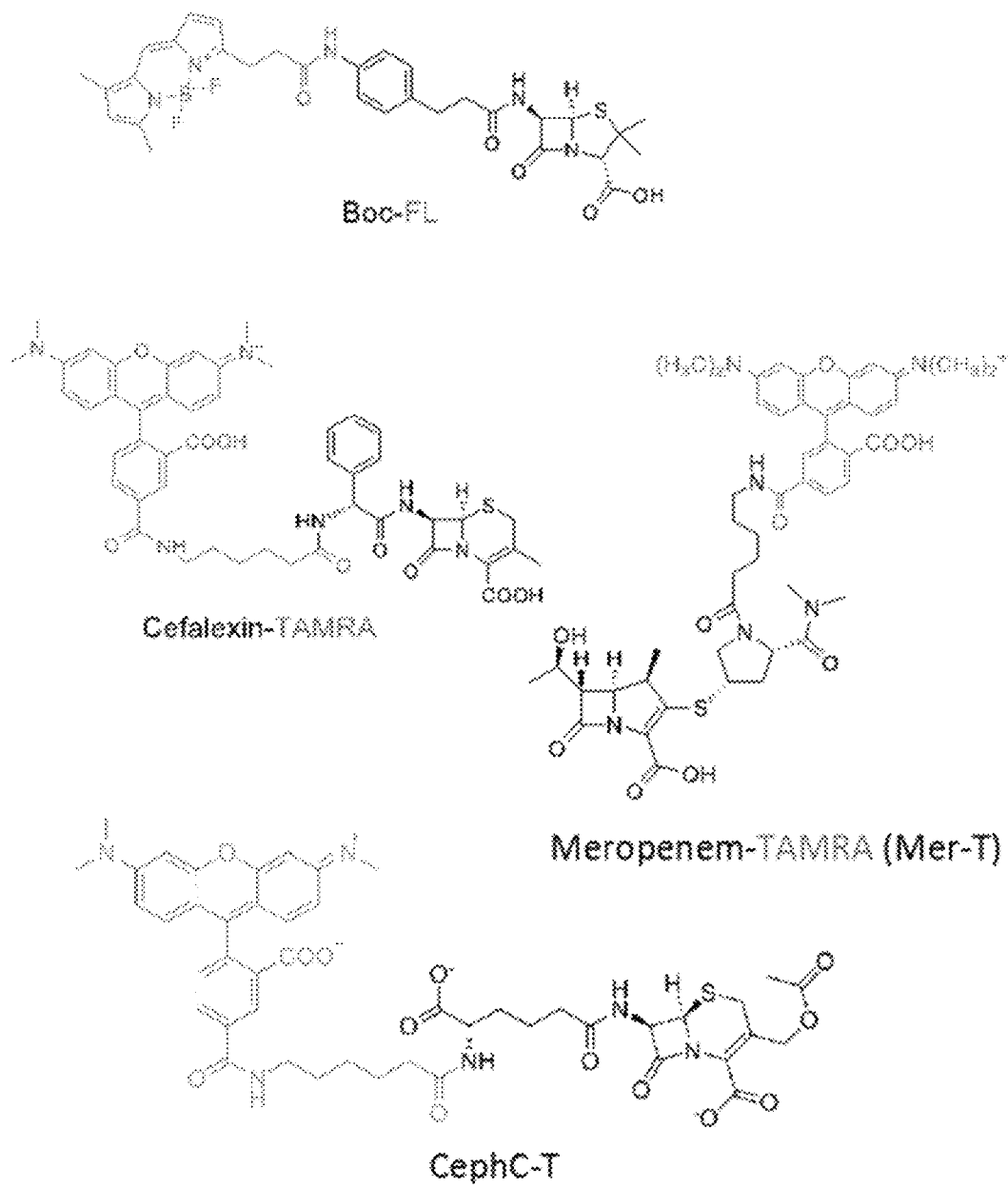
FIG. 1 shows structures of conjugates Boc-FL, cephalosporin C-TAMRA (CephC-T), Mer-T, and Cephalexin-T.
Figure 2:
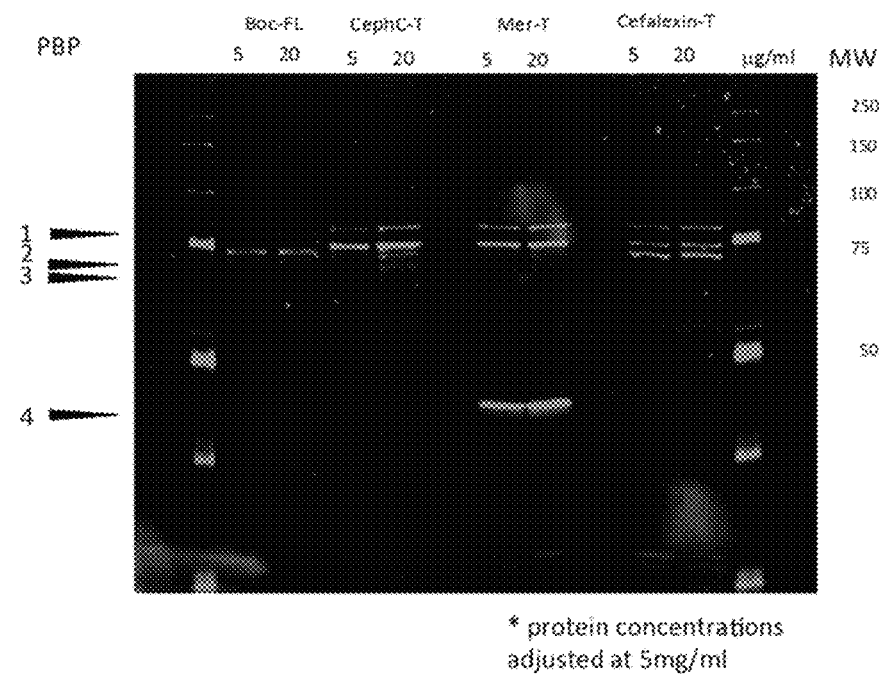
FIG. 2 shows gel-based analysis of the PBP profiles of *Staphylococcus aureus* BAA-1721 cells that are labeled with Boc-FL, CephC-T, Mer-T, or Cephalexin-T.
Figure 3:
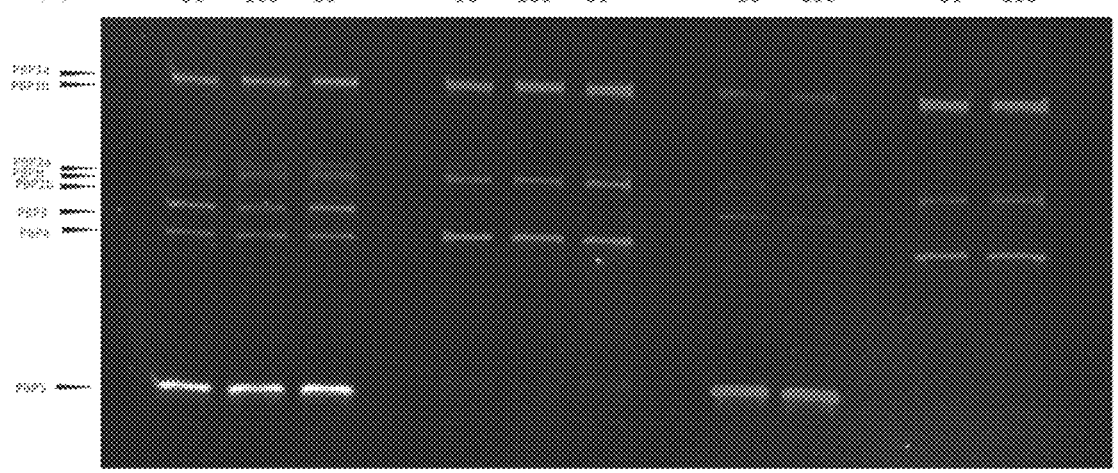
FIG. 3 shows gel-based analysis of the PBP profiles of *Bacillus subtilis* PY79 cells that are labeled with Boc-FL, Cephalexin-T, Mer-T, or CephC-T.
Figure 4:
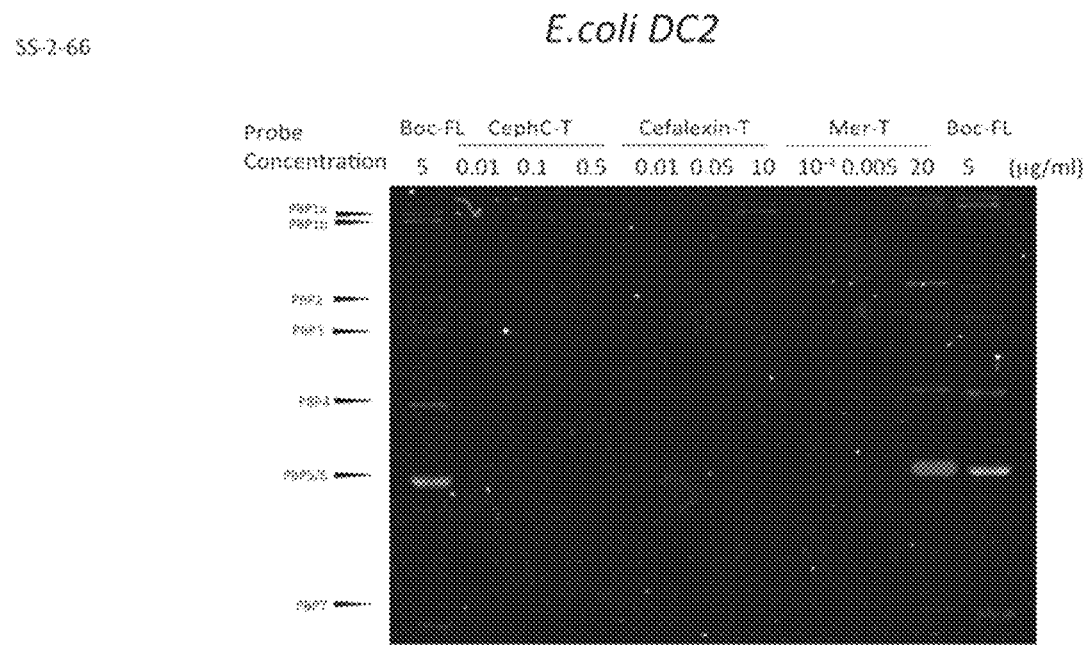
FIG. 4 shows gel-based analysis of the PBP profiles of *E. coli* DC2 cells that are labeled with Boc-FL, CephC-T, Cephalexin-T, or Mer-T.
Figure 5:
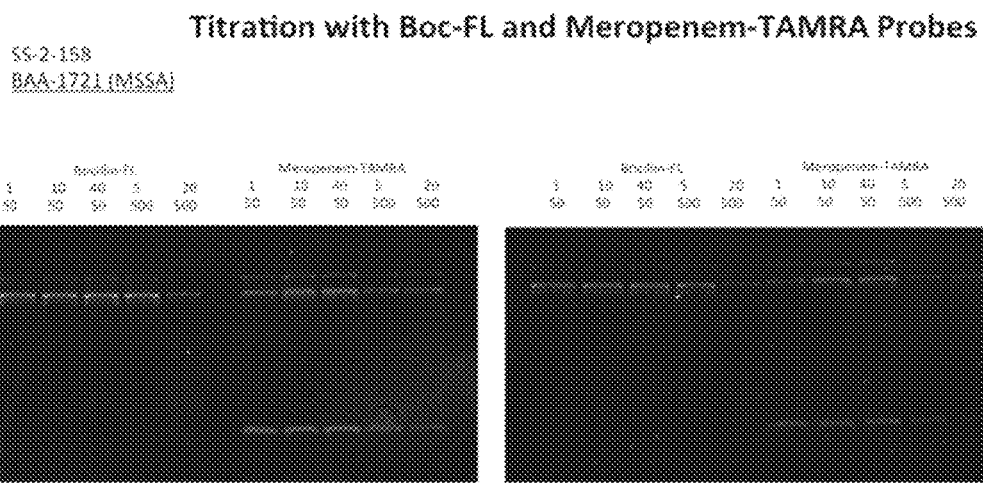
FIG. 5 shows labeling titration of *Staphylococcus aureus* BAA-1721 cells with Boc-FL or Mer-T.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $C_1-C_6$alkyl, $(C_2-C_6)$alkyl and $(C_3-C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkylene" by itself or as part of another substituent means a divalent radical derived from an alkane (including straight and branched alkanes), as exemplified by —$CH_2CH_2CH_2CH_2$— and —$CH(CH_3)CH_2CH_2$—. The term "alkenylene" means a divalent radical derived from an alkene (including straight and branched alkanes). The term "alkynylene" means a divalent radical derived from an alkyne (including straight and branched alkanes).

The term "alkoxy" refers to an alkyl group attached to the remainder of the molecule via an oxygen atom ("oxy").

The term "cycloalkyl" refers to a saturated all carbon ring having 3 to 8 carbon atoms (i.e., $(C_3-C_8)$carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbomane, bicyclo[2.2.2] octane, etc). Non-limiting examples of cycloalkyls include cyclopropyl, cyclobutyl, cyclopentyl, cyclohexyl, bicyclo [2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., cycloalkyl. Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-8 membered heterocycle. In one embodiment the term heterocycle includes a 3-6 membered heterocycle. In one embodiment the term heterocycle includes a 4-6 membered heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, and heteroaryl It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "aryloxy" refers to an aryl group attached to the remainder of the molecule via an oxygen atom ("oxy").

The term "heteroaryloxy" refers to an heteroaryl group attached to the remainder of the molecule via an oxygen atom ("oxy").

As used herein, the term "heteroatom" is meant to include oxygen (O), nitrogen (N), sulfur (S) and silicon (Si).

As used herein a wavy line "⌇" that intersects a bond in a chemical structure indicates the point of attachment of the bond that the wavy bond intersects in the chemical structure to the remainder of a molecule.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

A fluorescent group is also called a "fluorescent tag" or a "fluorophore". A fluorophore is a molecule that absorbs light (i.e., excites) at a characteristic wavelength and emits light (i.e. fluoresces and emits a signal) at a second lower-energy wavelength. The detectable agent may include, but is not limited to, one or more of the following fluorescent groups: fluorescein, tetrachlorofluorescein, hexachlorofluorescein, tetramethylrhodamine, rhodamine, cyanine-derivative dyes, Texas Red, Bodipy, and Alexa dyes. Examples of certain fluorophores are listed at www.researchservices.umn.edu/sites/researchservices.umn.edu/files/configuration-lsr-fortessa-h0081.pdf, which is incorporated by reference herein, which includes, e.g., FITC, GFP, 488 B, Brilliant Blue 515, CFSE, 7-AAD, PerCP, PerCP-Cy5-5, 488 A, PerCP-eFluor 710, SSC, APC-Cy7, APC-H7, 640A, APC-Alexa Fluor 750, APC-eFluor 780, Alexa Fluor 647, APC, 640 C, Sytox Red, Alexa Fluor 700, 640 B, Qdot 705, 405 B, Brilliant Violet 711, Qdot 605, 405 D, Brilliant Violet 605, eFluor 605, Pacific Blue, 405 F, Brilliant Violet 421, DyeCycle Violet, eFluor 450, Horizon v450, Qdot 800, 405 A, Brilliant Violet 786, Qdot 655, 405 C, Brilliant Violet 650, eFluor 650, Pacific Orange, 405 E, Brilliant Violet 510, Horizon v500, L/D Fixable Aqua, PE-Cy7, 561 A, DsRed, PE, 561 C, Cy3, tdTomato, PE-CF594, PE-Texas Red, PI, 561 B, mCherry, PE-Alexa Fluor, 355 B, Brilliant Ultraviolet 737, Alexa Fluor 350, 355 D, Brilliant Ultraviolet 395, 355 A, Brilliant Ultraviolet 805, 355 C and Brilliant Ultraviolet 496 . Characteristic absorption and emission wavelengths for each of these are well known to those of skill in the art.

In certain embodiments, the fluorophore is one or more of the fluorophores listed in Table 1.

TABLE 1

| Probe | Excitation (nm) | Emission (nm) |
| --- | --- | --- |
| Hydroxycoumarin | 325 | 386 |
| Alexa fluor | 325 | 442 |
| Aminocoumarin | 350 | 445 |
| Methoxycoumarin | 360 | 410 |
| Cascade Blue | (375); 401 | 423 |
| Pacific Blue | 403 | 455 |
| Pacific Orange | 403 | 551 |
| Lucifer yellow | 425 | 528 |
| Alexa fluor 430 | 430 | 545 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| Red 613 | 480; 565 | 613 |
| PerCP | 490 | 675 |
| Cy2 | 490 | 510 |
| TruRed | 490, 675 | 695 |
| FluorX | 494 | 520 |
| Fluorescein | 495 | 519 |
| FAM | 495 | 515 |
| BODIPY-FL | 503 | 512 |
| TET | 526 | 540 |
| Alexa fluor 532 | 530 | 555 |
| HEX | 535 | 555 |
| TRITC | 547 | 572 |
| Cy3 | 550 | 570 |
| TMR | 555 | 575 |
| Alexa fluor 546 | 556 | 573 |
| Alexa fluor 555 | 556 | 573 |
| Tamara | 565 | 580 |
| X-Rhodamine | 570 | 576 |
| Lissamine Rhodamine B | 570 | 590 |

TABLE 1-continued

| Probe | Excitation (nm) | Emission (nm) |
| --- | --- | --- |
| ROX | 575 | 605 |
| Alexa fluor 568 | 578 | 603 |
| Cy3.5 581 | 581 | 596 |
| Texas Red | 589 | 615 |
| Alexa fluor 594 | 590 | 617 |
| Alexa fluor 633 | 621 | 639 |
| LC red 640 | 625 | 640 |
| Allophycocyanin (APC) | 650 | 660 |
| Alexa fluor 633 | 650 | 688 |
| APC-Cy7 conjugates | 650; 755 | 767 |
| Cy5 | 650 | 670 |
| Alexa fluor 660 | 663 | 690 |
| Cy5.5 | 675 | 694 |
| LC red 705 | 680 | 710 |
| Alexa fluor 680 | 679 | 702 |
| Cy7 | 743 | 770 |
| IRDye 800 CW | 774 | 789 |
| Alexa Fluor 488 | 490 | 525 |
| Alexa Fluor 647 | 650 | 665 |
| Brilliant Violet 421 | 405 | 421 |

In certain in vivo embodiments, the fluorophore emits in the near infrared range, such as in the 650-900 nm range. (Weissleder et al., "Shedding light onto live molecular targets, *Nature Medicine,* 9:123-128 (2003)).

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Conjugates

In one embodiment, R comprises a moiety of formula (II) or formula (III):

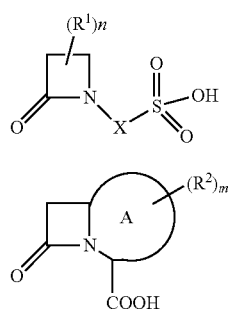

or a salt thereof, wherein X is absent or —O—;
ring A is a 5-6 membered heterocycle;
each $R^1$ is independently selected from the group consisting of hydrogen, hydroxy, halo, —CN, —NO$_2$, —SR$^a$, —NR$^a$R$^b$, —(C=O)R$^a$, —(C=O)OR$^a$, —O(C=O)R$^a$, —(C=O)NR$^a$R$^b$, —NR$^a$(C=O)R$^b$, (C$_1$-C$_8$)alkyl, (C$_2$-C$_8$)alkenyl, (C$_2$-C$_8$)alkynyl, 3-8 membered cycloalkyl and (C$_1$-C$_8$)alkoxy, wherein the (C$_1$-C$_8$)alkyl, (C$_2$-C$_8$)alkenyl, (C$_2$-C$_8$)alkynyl, 3-8 membered cycloalkyl and (C$_1$-C$_8$)alkoxy are optionally substituted with one or more groups independently selected from the group consisting of hydroxy, halo, —CN, —NO$_2$, —SR$^a$, —NR$^a$R$^b$, —(C=O)R$^a$, —(C=O)OR$^a$, —O(C=O)R$^a$, —(C=O)NR$^a$R$^b$, and —NR$^a$(C=O)R$^b$;

each $R^2$ is independently selected from the group consisting of hydrogen, hydroxy, halo, —CN, —NO$_2$, —SR$^c$, —NR$^c$R$^d$, —(C=O)R$^c$, —(C=O)OR$^c$, —O(C=O)R$^c$, —(C=O)NR$^c$R$^d$, —NR$^c$(C=O)R$^d$, (C$_1$-C$_8$)alkyl, (C$_2$-C$_8$)alkenyl, (C$_2$-C$_8$)alkynyl, 3-8 membered cycloalkyl, 3-8 membered heterocycle and (C$_1$-C$_8$)alkoxy, wherein the (C$_1$-C$_8$)alkyl, (C$_2$-C$_8$)alkenyl, (C$_2$-C$_8$)alkynyl, 3-8 membered cycloalkyl, 3-8 membered heterocycle and (C$_1$-C$_8$)alkoxy are optionally substituted with one or more groups independently selected from the group consisting of hydroxy, halo, —CN, —NO$_2$, —SR$^c$, —NR$^c$R$^d$, —(C=O)R$^c$, —(C=O)OR$^c$, —O(C=O)R$^c$, —(C=O)NR$^c$R$^d$, and —NR(C=O)R$^d$;

each $R^a$ is independently selected from the group consisting of hydrogen, (C$_1$-C$_8$)alkyl, (C$_2$-C$_8$)alkenyl, (C$_2$-C$_8$)alkynyl and 3-8 membered cycloalkyl, wherein the (C$_1$-C$_8$)alkyl, (C$_2$-C$_8$)alkenyl, (C$_2$-C$_8$)alkynyl and 3-8 membered cycloalkyl are optionally substituted with one or more groups independently selected from the group consisting of hydroxy, halo, —CN, —NO$_2$, —SH, -oxo- and —NH$_2$; each $R^b$ is independently selected from the group consisting of hydrogen, (C$_1$-C$_8$)alkyl, (C$_2$-C$_8$)alkenyl, (C$_2$-C$_8$)alkynyl and 3-8 membered cycloalkyl, wherein the (C$_1$-C$_8$)alkyl, (C$_2$-C$_8$)alkenyl, (C$_2$-C$_8$)alkynyl and 3-8 membered cycloalkyl are optionally substituted with one or more groups independently selected from the group consisting of hydroxy, halo, —CN, —NO$_2$, —SH, -oxo- and —NH$_2$; or $R^a$ and $R^b$ together with the nitrogen to which they are attached form a 3 to 8 membered heterocyclic ring that is optionally substituted with one or more groups independently selected from the group consisting of hydroxyl, halo and (C$_1$-C$_8$)alkyl;

each $R^c$ is independently selected from the group consisting of hydrogen, (C$_1$-C$_8$)alkyl, (C$_2$-C$_8$)alkenyl, (C$_2$-C$_8$)alkynyl and 3-8 membered cycloalkyl, wherein the (C$_1$-C$_8$)alkyl, (C$_2$-C$_8$)alkenyl, (C$_2$-C$_8$)alkynyl and 3-8 membered cycloalkyl are optionally substituted with one or more groups independently selected from the group consisting of hydroxy, halo, —CN, —NO$_2$, —SH, -oxo- and —NH$_2$; each $R^d$ is independently selected from the group consisting of hydrogen, (C$_1$-C$_8$)alkyl, (C$_2$-C$_8$)alkenyl, (C$_2$-C$_8$)alkynyl and 3-8 membered cycloalkyl, wherein the (C$_1$-C$_8$)alkyl, (C$_2$-C$_8$)alkenyl, (C$_2$-C$_8$)alkynyl and 3-8 membered cycloalkyl are optionally substituted with one or more groups independently selected from the group consisting of hydroxy, halo, —CN, —NO$_2$, —SH, -oxo- and —NH$_2$; or $R^c$ and $R^d$ together with the nitrogen to which they are attached form a 3 to 8 membered heterocyclic ring that is optionally substituted with one or more groups independently selected from the group consisting of hydroxyl, halo and (C$_1$-C$_8$)alkyl;

n is 0, 1 or 2;
m is 0, 1, 2, or 3; and
the moiety of formula (II) or (III) is linked to the rest of R at any synthetically feasible positions on the moiety of formula (II) or (III).

In one embodiment, the moiety of formula II is:

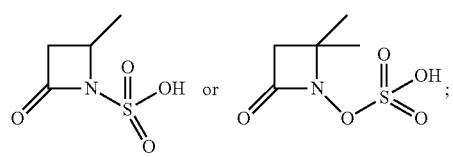

or a salt thereof.

In one embodiment, the moiety of formula III has the following formula:

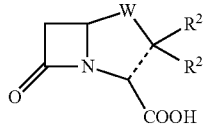

IIIa or a salt thereof, wherein

W is —O—, —S—, or —CR$^{X1}$R$^{X2}$;

R$^{X1}$ is selected from the group consisting of hydrogen, (C$_1$-C$_8$)alkyl, (C$_2$-C$_8$)alkenyl, (C$_2$-C$_8$)alkynyl, or 3-8 membered cycloalkyl, wherein the (C$_1$-C$_8$)alkyl, (C$_2$-C$_8$)alkenyl, (C$_2$-C$_8$)alkynyl, and 3-8 membered cycloalkyl are optionally substituted with one or more groups independently selected from hydroxy, halo, —CN, —NO$_2$, —SR$^e$, -oxo- and —NR$^e$R$^f$;

R$^{X2}$ is selected from the group consisting of hydrogen, (C$_1$-C$_8$)alkyl, (C$_2$-C$_8$)alkenyl, (C$_2$-C$_8$)alkynyl, or 3-8 membered cycloalkyl, wherein the (C$_1$-C$_8$)alkyl, (C$_2$-C$_8$)alkenyl, (C$_2$-C$_8$)alkynyl, and 3-8 membered cycloalkyl are optionally substituted with one or more groups independently selected from hydroxy, halo, —CN, —NO$_2$, —SR$^e$, -oxo- and —NR$^e$R$^f$;

each R$^e$ is independently selected from the group consisting of hydrogen, (C$_1$-C$_8$)alkyl, (C$_2$-C$_8$)alkenyl, (C$_2$-C$_8$)alkynyl and 3-8 membered cycloalkyl, wherein the (C$_1$-C$_8$)alkyl, (C$_2$-C$_8$)alkenyl, (C$_2$-C$_8$)alkynyl and 3-8 membered cycloalkyl are optionally substituted with one or more groups independently selected from the group consisting of hydroxy, halo, —CN, —NO$_2$, —SH, -oxo- and —NH$_2$; each R$^f$ is independently selected from the group consisting of hydrogen, (C$_1$-C$_8$)alkyl, (C$_2$-C$_8$)alkenyl, (C$_2$-C$_8$)alkynyl and 3-8 membered cycloalkyl, wherein the (C$_1$-C$_8$)alkyl, (C$_2$-C$_8$)alkenyl, (C$_2$-C$_8$)alkynyl and 3-8 membered cycloalkyl are optionally substituted with one or more groups independently selected from the group consisting of hydroxy, halo, —CN, —NO$_2$, —SH, -oxo- and —NH$_2$; or R$^e$ and R$^f$ together with the nitrogen to which they are attached form a 3 to 8 membered heterocyclic ring that is optionally substituted with one or more groups independently selected from the group consisting of hydroxyl, halo and (C$_1$-C$_8$)alkyl; and the dash bond is a single bond or a double bond;

provided that when the dash bond is a double bond, one of R$^2$ is absent.

In one embodiment, the moiety of formula III has the following formula:

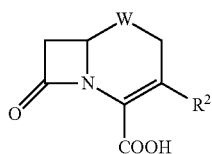

IIIb or a salt thereof, wherein

W is —O—, —S—, or —CR$^{X1}$R$^{X2}$—;

R$^{X1}$ is selected from the group consisting of hydrogen, (C$_1$-C$_8$)alkyl, (C$_2$-C$_8$)alkenyl, (C$_2$-C$_8$)alkynyl, or 3-8 membered cycloalkyl, wherein the (C$_1$-C$_8$)alkyl, (C$_2$-C$_8$)alkenyl, (C$_2$-C$_8$)alkynyl, and 3-8 membered cycloalkyl are optionally substituted with one or more groups independently selected from hydroxy, halo, —CN, —NO$_2$, —SR$^e$, -oxo- and —NR$^e$R$^f$;

R$^{X2}$ is selected from the group consisting of hydrogen, (C$_1$-C$_8$)alkyl, (C$_2$-C$_8$)alkenyl, (C$_2$-C$_8$)alkynyl, or 3-8 membered cycloalkyl, wherein the (C$_1$-C$_8$)alkyl, (C$_2$-C$_8$)alkenyl, (C$_2$-C$_8$)alkynyl, and 3-8 membered cycloalkyl are optionally substituted with one or more groups independently selected from hydroxy, halo, —CN, —NO$_2$, —SR$^e$, -oxo- and —NR$^e$R$^f$;

each R$^e$ is independently selected from the group consisting of hydrogen, (C$_1$-C$_8$)alkyl, (C$_2$-C$_8$)alkenyl, (C$_2$-C$_8$)alkynyl and 3-8 membered cycloalkyl, wherein the (C$_1$-C$_8$)alkyl, (C$_2$-C$_8$)alkenyl, (C$_2$-C$_8$)alkynyl and 3-8 membered cycloalkyl are optionally substituted with one or more groups independently selected from the group consisting of hydroxy, halo, —CN, —NO$_2$, —SH, -oxo- and —NH$_2$; and each R$^f$ is independently selected from the group consisting of hydrogen, (C$_1$-C$_8$)alkyl, (C$_2$-C$_8$)alkenyl, (C$_2$-C$_8$)alkynyl and 3-8 membered cycloalkyl, wherein the (C$_1$-C$_8$)alkyl, (C$_2$-C$_8$)alkenyl, (C$_2$-C$_8$)alkynyl and 3-8 membered cycloalkyl are optionally substituted with one or more groups independently selected from the group consisting of hydroxy, halo, —CN, —NO$_2$, —SH, -oxo- and —NH$_2$; or R$^e$ and R$^f$ together with the nitrogen to which they are attached form a 3 to 8 membered heterocyclic ring that is optionally substituted with one or more groups independently selected from the group consisting of hydroxyl, halo and (C$_1$-C$_8$)alkyl.

In one embodiment, W is —O—, —S—, or —CH$_2$—.

In one embodiment, each R$^2$ is independently hydrogen, (C$_1$-C$_8$)alkyl, —SR$^c$, or 3-8 membered heterocycle.

In one embodiment, R is selected from the group consisting of:

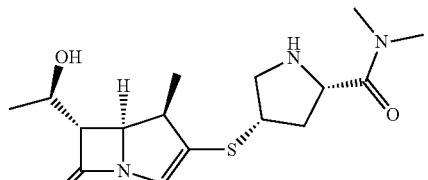

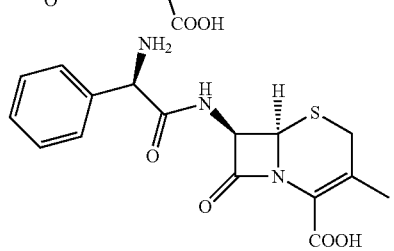

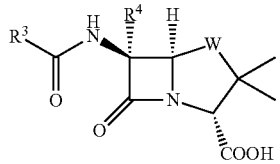

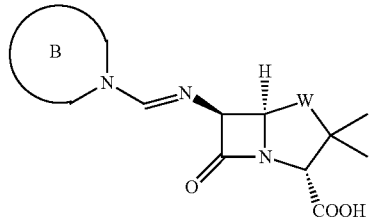

-continued

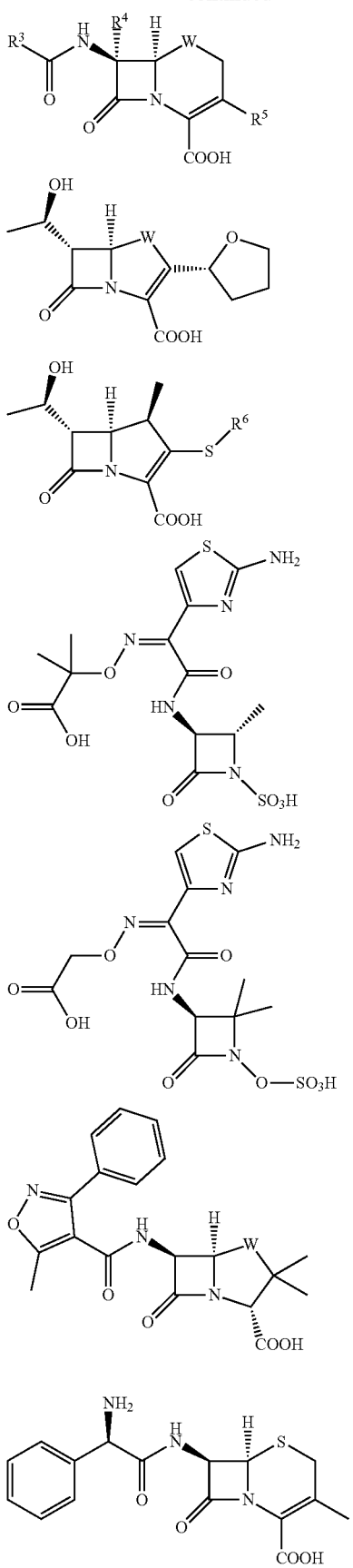

-continued

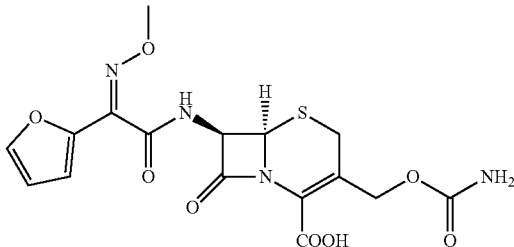

and salts thereof, wherein:

W is —O—, —S—, or —CH$_2$—;

ring B is a 5-7 membered heterocyle;

R$^3$ is (C$_1$-C$_8$)alkyl, (C$_2$-C$_8$)alkenyl, (C$_2$-C$_8$)alkynyl, or 3-8 membered cycloalkyl, 4-8 membered heterocycle, aryl, or heteroaryl, wherein the (C$_1$-C$_8$)alkyl, (C$_2$-C$_8$)alkenyl, and (C$_2$-C$_8$)alkynyl are optionally substituted with aryl, heteroaryl, aryloxy or heteroaryloxy, wherein the aliphatic and aromatic portions of R$^3$ are optionally substituted with one or more groups independently selected from halo, —CN, —NO$_2$, OR$^g$, —SR$^g$, -oxo- and —N(R$^g$)$_2$;

R$^4$ is hydrogen, halo, (C$_1$-C$_4$)alkyl, or (C$_1$-C$_4$)alkyloxy;

R$^5$ is hydrogen, halo, (C$_1$-C$_8$)alkyl, (C$_2$-C$_8$)alkenyl, (C$_2$-C$_8$)alkynyl, or 3-8 membered cycloalkyl, 4-8 membered heterocycle, aryl, or heteroaryl, wherein the (C$_1$-C$_8$)alkyl, (C$_2$-C$_8$)alkenyl, and (C$_2$-C$_8$)alkynyl are optionally substituted with aryl, heteroaryl, aryloxy or heteroaryloxy, wherein the aliphatic and aromatic portions of R$^5$ are optionally substituted with one or more groups independently selected from halo, —CN, —NO$_2$, OR$^h$, —SR$^h$, -oxo- and —N(R$^h$)$_2$;

R$^6$ is hydrogen, (C$_1$-C$_8$)alkyl, (C$_2$-C$_8$)alkenyl, (C$_2$-C$_8$)alkynyl, or 3-8 membered cycloalkyl, 4-8 membered heterocycle, aryl, or heteroaryl, wherein the (C$_1$-C$_8$)alkyl, (C$_2$-C$_8$)alkenyl, and (C$_2$-C$_8$)alkynyl are optionally substituted with aryl, heteroaryl, aryloxy or heteroaryloxy, wherein the aliphatic and aromatic portions of R$^6$ are optionally substituted with one or more groups independently selected from halo, —CN, —NO$_2$, OR$^i$, —SR$^i$, -oxo- and —N(R$^i$)$_2$;

each R$^g$ is independently hydrogen or (C$_1$-C$_4$)alkyl;

each R$^h$ is independently hydrogen or (C$_1$-C$_4$)alkyl;

each R$^i$ is independently hydrogen or (C$_1$-C$_4$)alkyl; and

R is linked to L at any synthetically feasible position of R.

In one embodiment, R is selected from the group consisting of:

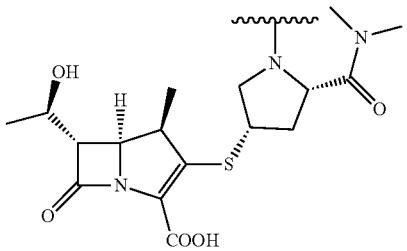

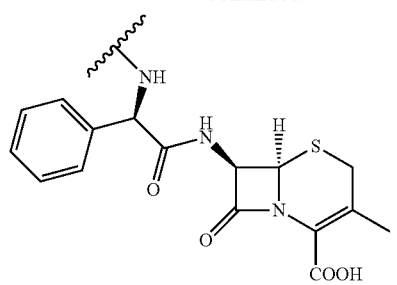
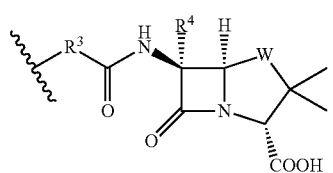
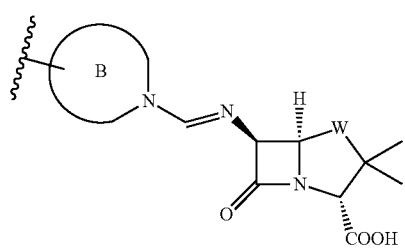
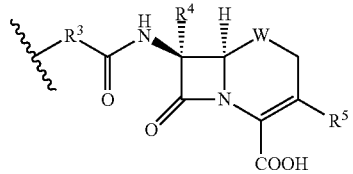
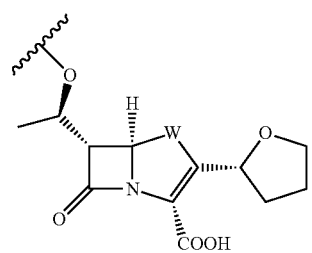
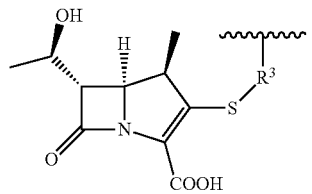
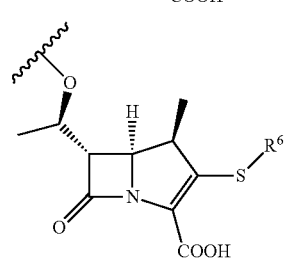
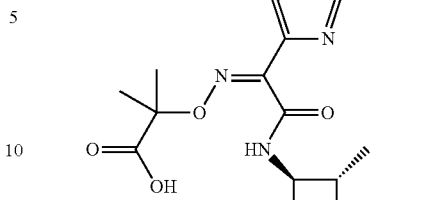
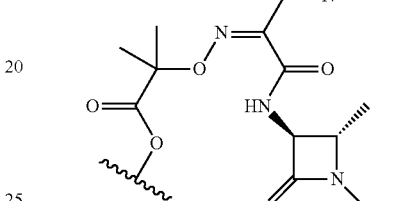
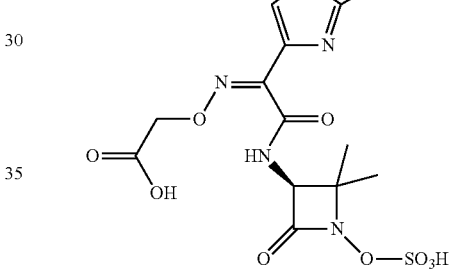
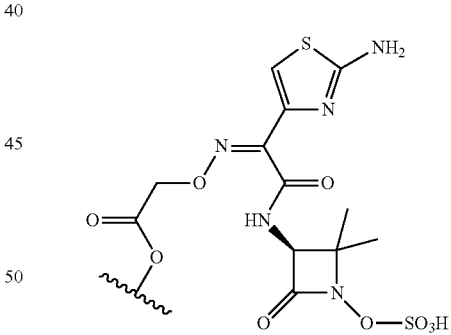
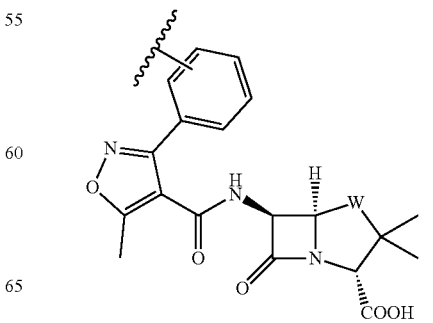

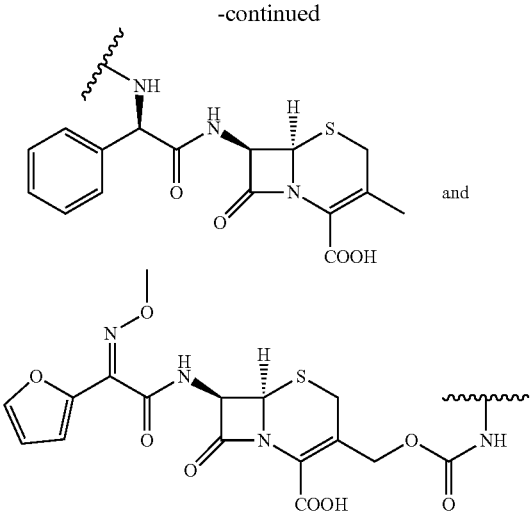

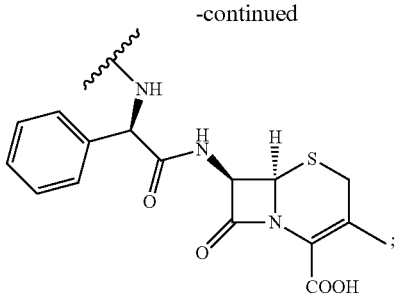

or a salt thereof.

In one embodiment, the antibiotic is selected from the group consisting of faropenem, doripenem, meropenem, (+)-6-aminopenicillanic acid (6-APA), ampicillin, ethicillin, amdinocillin (mecillinam), oxacillin, cloxacillin, dicloxacillin, piperacillin, cephalexin, cefsulodin, cefoxitin, cephalothin, cefuroxime, ceftriaxone, cefotaxime, aztreonam and amoxicillin.

In one embodiment of the invention the linking group has a molecular weight of from about 20 daltons to about 20,000 daltons.

In one embodiment, the linking group has a molecular weight of from about 20 daltons to about 5,000 daltons.

In one embodiment, the linking group has a molecular weight of from about 20 daltons to about 1,000 daltons.

In one embodiment, the linking group has a molecular weight of from about 20 daltons to about 200 daltons.

In another embodiment, the linking group has a length of about 5 angstroms to about 60 angstroms.

In another embodiment, the linking group separates the antibiotic from the remainder of the conjugate of formula I by about 5 angstroms to about 40 angstroms, inclusive, in length.

In another embodiment, the linking group is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment, L is independently a divalent, branched or unbranched, saturated or unsaturated, hydrocarbon chain, having from 1 to 20 carbon atoms, wherein one or more of the carbon atoms in the hydrocarbon chain is optionally replaced by —O—, —$NR^{L-}$, or —S—; wherein $R^L$ is hydrogen or $(C_1-C_6)$alkyl; wherein the hydrocarbon chain, is optionally substituted with one or more substituents selected from halo, hydroxyl, $(C_1-C_6)$alkoxy, and oxo (=O).

In one embodiment, L is:

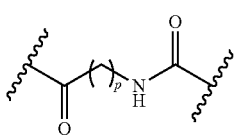

wherein p is 1, 2, 3, 4, 5, 6, 7, 8, 9 or 10.

In one embodiment, L is
—C(=O)$(CH_2)_5$NHC(=O)—.

and salts thereof, wherein:

W is —O—, —S—, or —$CH_2$—;

ring B is a 5-7 membered heterocyle;

$R^3$ is $(C_1-C_8)$alkylene, $(C_2-C_8)$alkenylene, $(C_2-C_8)$alkynylene, or 3-8 membered cycloalkyl, 4-8 membered heterocycle, aryl, or heteroaryl, wherein the $(C_1-C_8)$alkylene, $(C_2-C_8)$alkenylene, and $(C_2-C_8)$alkynylene are optionally substituted with aryl, heteroaryl, aryloxy or heteroaryloxy, wherein the aliphatic and aromatic portions of $R^3$ are optionally substituted with one or more groups independently selected from halo, —CN, —$NO_2$, $OR^g$, —$SR^g$, -oxo- and —$N(R^g)_2$;

$R^4$ is hydrogen, halo, $(C_1-C_4)$alkyl, or $(C_1-C_4)$alkyloxy;

$R^5$ is hydrogen, halo, $(C_1-C_8)$alkyl, $(C_2-C_8)$alkenyl, $(C_2-C_8)$alkynyl, or 3-8 membered cycloalkyl, 4-8 membered heterocycle, aryl, or heteroaryl, wherein the $(C_1-C_8)$alkyl, $(C_2-C_8)$alkenyl, and $(C_2-C_8)$alkynyl are optionally substituted with aryl, heteroaryl, aryloxy or heteroaryloxy, wherein the aliphatic and aromatic portions of $R^5$ are optionally substituted with one or more groups independently selected from halo, —CN, —$NO_2$, $OR^h$, —$SR^h$, -oxo- and —$N(R^h)_2$;

$R^6$ is hydrogen, $(C_1-C_8)$alkyl, $(C_2-C_8)$alkenyl, $(C_2-C_8)$alkynyl, or 3-8 membered cycloalkyl, 4-8 membered heterocycle, aryl, or heteroaryl, wherein the $(C_1-C_8)$alkyl, $(C_2-C_8)$alkenyl, and $(C_2-C_8)$alkynyl are optionally substituted with aryl, heteroaryl, aryloxy or heteroaryloxy, wherein the aliphatic and aromatic portions of $R^6$ are optionally substituted with one or more groups independently selected from halo, —CN, —$NO_2$, $OR^i$, —$SR^i$, -oxo- and —$N(R^i)_2$;

each $R^g$ is independently hydrogen or $(C_1-C_4)$alkyl;
each $R^h$ is independently hydrogen or $(C_1-C_4)$alkyl; and
each $R^i$ is independently hydrogen or $(C_1-C_4)$alkyl.

In one embodiment, R is:

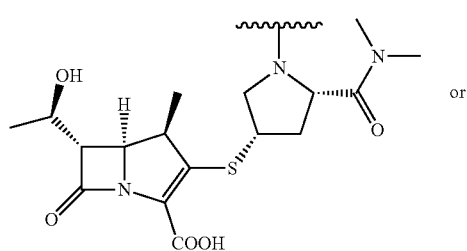

In one embodiment, Y is 3-8 membered cycloalkyl comprising at least one triple bond, 1,2,4,5-tetrazinyl which is optionally substituted with $(C_1-C_8)$alkyl, a fluorescent group, or biotin.

In one embodiment, Y is a fluorescent group.

In one embodiment, Y comprises a core structure selected from the group consisting of coumarin, hydroxyphenylquinazolinone (HPQ), dicyanomethylenedihydrofuran (DCDHF), fluorescein, carboxyfluorescein, rhodol, rhodamine, carboxytetramethylrhodamine (TAMRA), rosamine, boron-dipyrromethene (BODIPY), resorufin, acridinone, and indocarbocyanine, and an analog thereof.

In one embodiment, Y is BODIPY or TAMRA.

In one embodiment, Y is

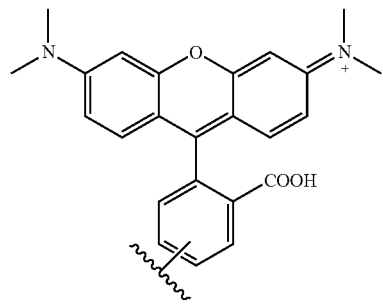

or a salt thereof.

One embodiment of the invention provides a conjugate of formula I which is:

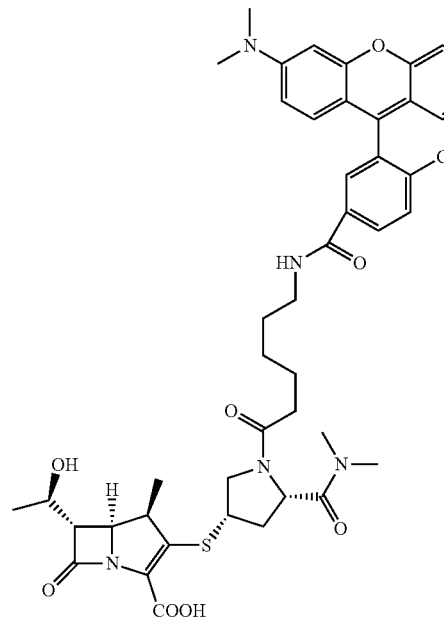

or

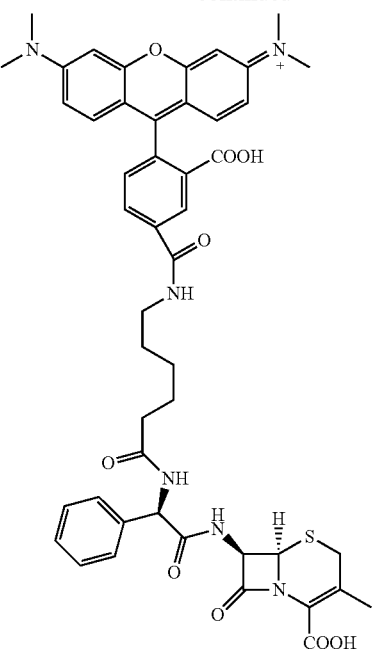

or a salt thereof.

One embodiment of the invention provides a conjugate of formula I which is:

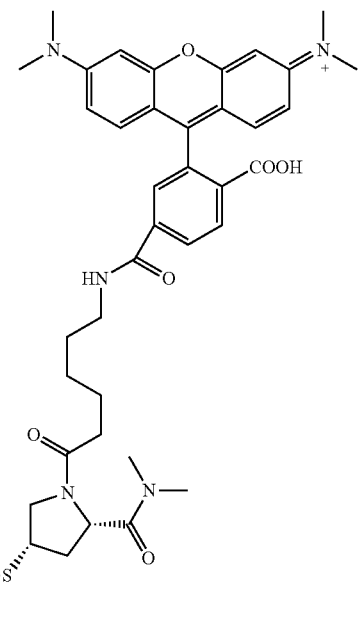

or a salt thereof.

One embodiment of the invention provides a conjugate of formula I which is not:

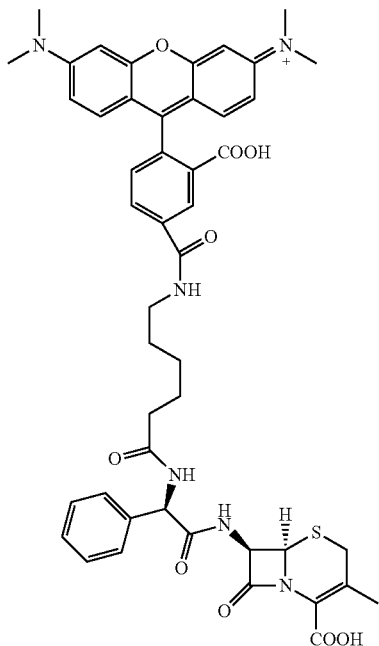

or a salt thereof.

Methods of Use

Certain embodiments of the invention provide a method for labeling one or more penicillin-binding proteins (PBPs) comprising contacting a cell with a conjugate of formula I or a salt thereof, wherein the conjugate binds to the one or more PBPs.

Certain embodiments of the invention provide a method for labeling one or more penicillin-binding proteins (PBPs) comprising contacting a cell fraction comprising one or more PBPs with a conjugate of formula I or a salt thereof, wherein the conjugate binds to the one or more PBPs.

In one embodiment, more than one PBPs are labeled.

In one embodiment, the labeled PBPs are different.

In one embodiment, the cell fraction is purified cell membranes.

In one embodiment, the one or more PBPs are labeled in vivo.

In one embodiment, the one or more PBPs are labeled in vitro.

Certain embodiments of the invention provide a method for labeling one or more penicillin-binding proteins (PBPs) comprising contacting a cell or a cell fraction comprising one or more PBPs with a conjugate of formula I or a salt thereof and detecting the one or more labeled PBPs, wherein the conjugate binds to the one or more PBPs.

In one embodiment, the one or more labeled PBPs are detected by SDS-PAGE.

In one embodiment, the one or more labeled PBPs are detected by microscopy.

Certain embodiments of the invention provide a method for labeling one or more penicillin-binding proteins (PBPs) comprising contacting a cell or a cell fraction comprising one or more PBPs with a conjugate of formula I or a salt thereof, detecting the one or more labeled PBPs, and staining the cell membrane with a dye wherein the conjugate binds to the one or more PBPs.

In one embodiment, the dye is N-(3-triethylammonium-propyl)-4-(6-(4-(diethylamino)phenyl)hexatrienyl)pyridinium dibromide or 1-(4-trimethylammoniumphenyl)-6-phenyl-1,3,5-hexatriene p-toluensulfonate (TMA-DPH).

Certain embodiments of the invention provide a method for labeling one or more penicillin-binding proteins (PBPs) comprising contacting a cell or a cell fraction comprising one or more PBPs with a conjugate of formula I or a salt thereof and isolating the one or more labeled PBPs, wherein the conjugate binds to the one or more PBPs.

Certain embodiments of the invention provide a method for labeling one or more penicillin-binding proteins (PBPs) comprising contacting a cell or a cell fraction comprising one or more PBPs with a conjugate of formula I or a salt thereof, isolating the one or more labeled PBPs, and identifying the one or more labeled PBPs, wherein the conjugate binds to the one or more PBPs.

In one embodiment, the one or more labeled PBPs are identified by liquid chromatography-mass spectrometry (LC-MS).

In one embodiment, the one or more PBPs are selected from the group consisting of class A high molecular weight PBPs, class B high molecular weight PBPs and low molecular weight PBPs.

In one embodiment, the cell or cell fraction is a gram positive bacteria cell or a gram positive bacteria cell fraction.

In one embodiment, the gram positive bacteria is selected from the group consisting of *Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Micrococcus luteus, Mycobacterium tuberculosis, Bacillus anthracis, Bacillus cereus, Clostridium difficile, Propionibacterium acnes, Streptococcus mutans, Actinomyces viscosus, Actinomyces naeslundii, Streptococcus sanguis, Streptococcus pneumoniae, Listeria monocytogenes* and *Streptococcus salivarius*.

In one embodiment, the cell or cell fraction is a gram negative bacteria cell or a gram negative bacteria cell fraction.

In one embodiment, the gram negative bacteria is selected from the group consisting of *Escherchia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitidis* and *Haemophilus influenzae*.

Certain embodiments of the invention provides a method for detecting the PBP affinity of a conjugate of formula I:

1) incubating a cell or a cell fraction comprising one or more PBPs with a conjugate of formula I, or a salt thereof, to selectively label PBPs in the cell or the cell fraction:

2) incubating the cell or the cell fraction with BOCILLIN-FL to label the remaining PBPs in the cell:

3) detecting the labeled PBPs from steps 1) and 2).

In one embodiment, the cell fraction is purified cell membrane.

In one embodiment, the one or more PBPs are labeled in vivo.

In one embodiment, the one or more PBPs are labeled in vitro.

In one embodiment, the one or more PBPs are detected by SDS-PAGE.

In one embodiment, the one or more PBPs are detected by microscopy.

Certain embodiments of the invention provides a method for detecting the PBP affinity of a conjugate of formula I:

1) incubating a cell or a cell fraction comprising one or more PBPs with a conjugate of formula I, or a salt thereof, to selectively label PBPs in the cell or the cell fraction;

2) incubating the cell or the cell fraction with BOCILLIN-FL to label the remaining PBPs in the cell;

3) detecting the labeled PBPs from steps 1) and 2); and 4) staining the cell membrane with a dye.

Certain embodiments of the invention provide a method for inhibiting one or more PBPs, comprising contacting one or more PBPs with a conjugate of formula I, or a salt thereof.

Kits

Certain embodiments of the invention provide a kit comprising:

1) a conjugate of formula I or a salt thereof;

2) instructions for contacting a cell or a cell fraction comprising one or more penicillin-binding protein (PBPs) with the conjugate to label one or more PBPs; and 3) instructions for detecting the labeled PBPs.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Conjugates of invention can be prepared using known methods (Kocaoglu, O., et al. ACS Chem. Biol. 2012, 7, 1746-1753) or using procedures analogous to those described in the examples herein. For example, compounds of invention can be prepared as illustrated in the following scheme.

Synthesis

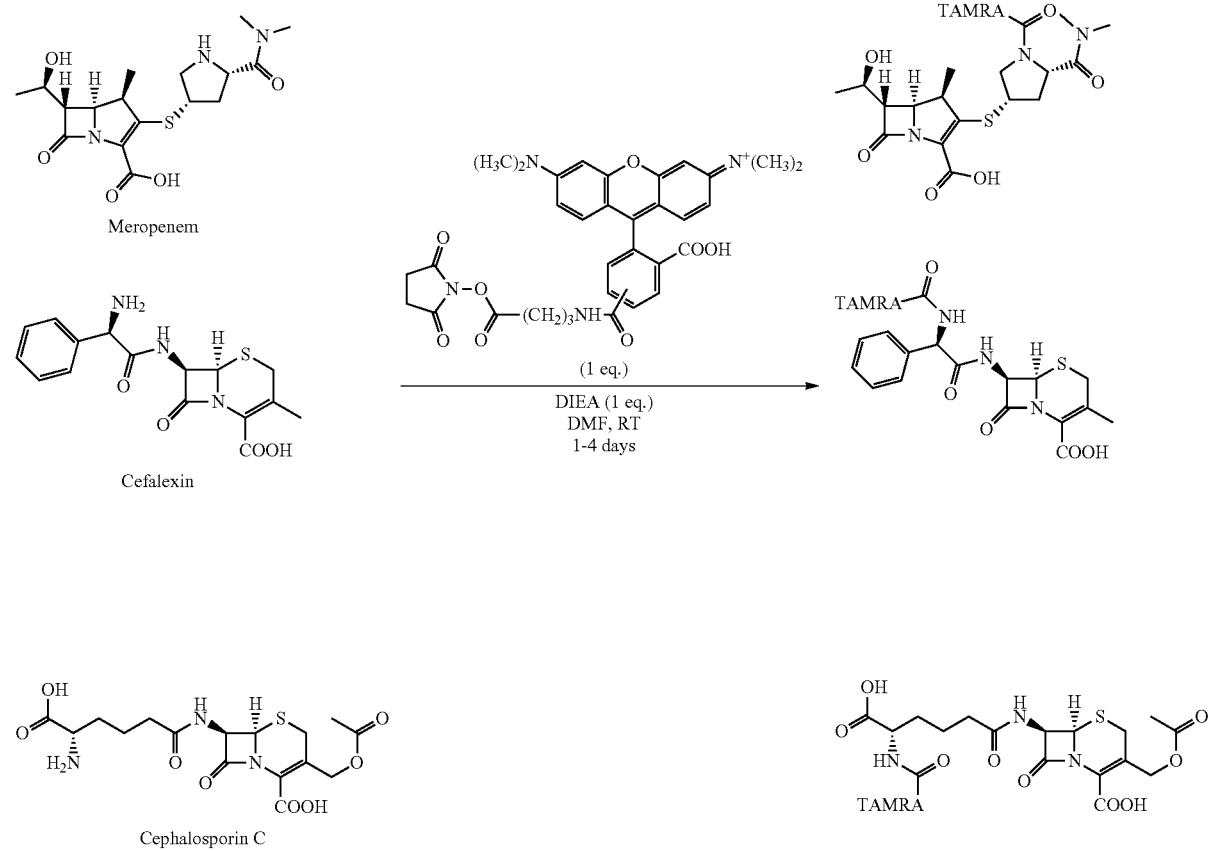

The invention will now be illustrated by the following non-limiting Examples.

EXAMPLES

Example 1. Synthesis of Conjugates

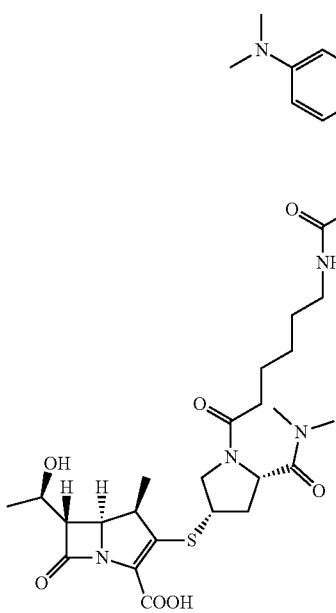

Meropenem-TAMRA (Mer-T)

Meropenem trihydrate (4.6 mg, 0.0105 mmol, 1.2 equiv) was dissolved in 100 μL anhydrous DMF. The resulting solution was further dried by addition of ~50 mg anhydrous magnesium sulfate powder and incubation for 10 min at room temperature. The solution was pipetted through glass wool and transferred to a 1 mL reaction vial under Argon. Anhydrous diisopropylethylamine, DIEA, (1.4 μL, 0.0085 mmol, 1.0 equiv) was added to the mixture. 6-(Tetramethylrhodamine-5-(and-6)-Carboxamido) Hexanoic Acid, Succinimidyl Ester), mixed isomers (5.0 mg, 0.0085 mmol, 1.0 equiv) in 50 μL anhydrous DMF, was added and the mixture was stirred under argon at room temperature. After 98 h, an additional equivalent of meropenem and DIEA was added and the reaction was stirred overnight. DMF was removed in vacuo to decrease the volume to ~50 μL, which was diluted with 50 μL water:acetonitrile (1:1) and purified using the described HPC method to yield 5.0 mg of product (74% yield). Final product was characterized by LC/MS (m/z): [M+H]+ calcd for $C_{48}H_{57}N_6O_{10}S^+$ 909.3851; found 909.3854.

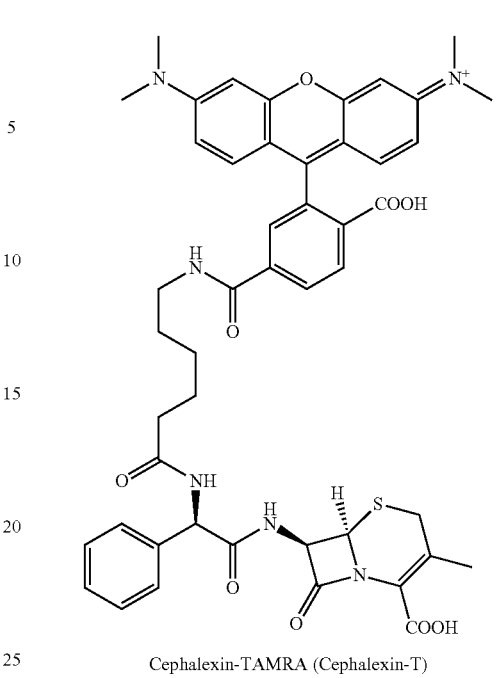

Cephalexin-TAMRA (Cephalexin-T)

Cephalexin hydrate (4.0 mg, 0.011 mmol, 1.4 equiv) was dissolved in 100 μL anhydrous DMF and dried over MgSO₄ as above. The solution was pipetted through glass wool and transferred to a 1 mL reaction vial under Argon. Anhydrous diisopropylethylamine, DIEA, (1.4 mL, 0.0085 mmol, 1.0 equiv) was added to the mixture. 6-(Tetramethylrhodamine-5-(and-6)-Carboxamido) Hexanoic Acid, Succinimidyl Ester), mixed isomers (5.0 mg, 0.0085 mmol, 1.0 equiv) in 50 μL anhydrous DMF, was added and the mixture was stirred under argon at room temperature. After 73 h, an additional equivalent of meropenem and base were added and the reaction was stirred overnight. DMF was removed in vacuo to decrease the volume to ~50 μL, which was diluted with 50 μL water:acetonitrile (1:1) and purified using the described HPC method to yield 4.0 mg of product (54% yield). Final product was characterized by LC/MS (m/z): [M+H]+ calcd for $C_{47}H_{49}N_6O_9S^+$ 873.3276; found 873.3286.

HPLC Conditions

Purification was performed using an acetonitrile:water gradient 5:95 to 95:5 containing 0.1% formic acid as modifier over 20 min; 1.5 mL/min reverse-phase C18 column (250×21 mm); 540 nm detection (for TAMRA fluorophore).

Example 2. Biological Assays, Such as In Vivo Labeling. Fluorescence Imaging. And Detecting PBP Affinity Probe Concentration Determination Probes were stored as DMSO solutions at −80° C. Concentrations were determined by measuring the UV-Vis absorption of each solution at the $\lambda_{max}$ of its corresponding fluorophore. For TAMRA-containing probes (ε=87,000 $M^{-1} \cdot cm^{-1}$), 10× and 100× dilutions of probe was made in methanol and absorbance was read at 543 nm using a NanoPhotometer P330 (IMPLEN).

*Streptococcus pneumoniae* Growth and Probe Labeling

*S. pneumoniae* strain IU1945, an unencapsulated derivative of serotype 2 strain D39, was grown statically in brain heart infusion (BHI) medium in 100×17 mm tubes by incubation in an atmosphere of 5% $CO_2$ at 37° C. to an $OD_{620}$ of ~0.2. For labeling experiments, overnight cultures that were still in exponential phase ($OD_{620}$=0.1-0.4) were diluted to $OD_{620}$=0.002-0.004 and grown as above. Samples with $OD_{620}$=0.15-0.20 were utilized in labeling experiments conducted as previously described, (Kocaoglu, O., Carlson, E. E. Curr. Prot. Chem. Biol. 2014, 5(4): 239-250) and summarized as follows: Cell pellets from 1.5 mL cultures were harvested by centrifugation (16,100×g for 2 min at RT) and washed with phosphate buffered saline (PBS; pH 7.4). Cell pellets were resuspended in 50 µL of PBS containing the indicated concentrations for each probe and incubated at room temperature (RT) for 20 min, unless noted otherwise. A reference sample was suspended in 50 µL of PBS containing 5 µg/mL Boc-FL and incubated for 10 min at RT. The cells were washed and resuspended in 100 µl of PBS containing 10 mg/mL of lysozyme and were incubated for 30 min at 37° C. The cells were lysed by a Hielscher vial tweeter UP200St (70% C, 95% A, 5% adjustment snap and is SD Interval/10 s for 6×1 min intervals with 1 min cooling time in between), and the membrane proteome was isolated by centrifugation at 21,000×g for 15 min at 4° C. Membrane proteome was resuspended in 100 µL PBS, and the protein concentration was adjusted to 2.5 mg/mL by diluting with PBS. Thirty microliters of proteome sample was dispensed into a clean 1.5-mL microcentrifuge tube and 10 µL of 4×SDS-PAGE loading buffer was added to each sample. The samples were heated for 5 min at 90-95° C. and then cooled down to RT. Ten to twelve microliters of sample were loaded onto a 10% SDS-PAGE gel (acrylamide:bis-acrylamide=29:1). The protein bands were separated by gel electrophoresis for 1.5 h at 180 V, 400 mA, 60 W. The gel was rinsed with distilled water before fluorescence scanning. The same growth and labeling procedures were utilized with other microorganisms with minimal differences, as follows.

*E. coli:*

DC2 strain was grown in LB media at 37° C., while shaking at 150-220 rpm. Overnight cultures were diluted 10× in fresh LB and incubated under the same conditions to reach an $OD_{600}$~0.4-0.5 after which cells were harvested by centrifugation at 8,000×g for 2 min at RT. The same centrifugation settings were used throughout the assay, up to the lysis step.

*Bacillus subtilis:*

PY79 strain was grown in LB media at 37° C., while shaking at 150-220 rpm. Overnight cultures were diluted 1 Ox in fresh LB and incubated under the same conditions to reach an $OD_{600}$~0.4-0.5 after which cells were harvested by centrifugation using the same settings as for *S. pneumoniae*.

*Staphylococcus aureus:*

Methicillin-sensitive BAA-1721 strain was grown in tryptic soy broth (TSB) media at 37° C., while shaking at 150-220 rpm. Overnight cultures were diluted 10× in fresh TSB, incubated using the same conditions to reach an $OD_{600}$ ~0.4 after which cells were harvested by centrifugation using the same settings as for *S. pneumoniae*.

Sodium Dodecyl Sulfate-Polyacrylamide Gel Electrophoresis (SDS-PAGE)

The protocol for SDS-PAGE gel preparation was previously described (Kocaoglu, O., Carlson, E. E. Curr. Prot. Chem. Biol. 2014, 5(4): 239-250.). Briefly, polyacrylamide gels were composed of 10% resolving gel (10.5 ml of 1.5 M Tris-HCl buffer pH 8.8, 10.5 ml of acrylamide:bis-acrylamide 29:1 (40% solution), 21 ml of $H_2O$, 140 µl of 10% APS, 15 µl of tetramethylethylenediamine (TEMED)) and 4.5% stacking gel (2.5 ml of 0.5 M Tris-HCl buffer pH 6.8, 1.125 ml of acrylamide:bis-acrylamide 29:1 (40% solution), 6.375 ml of $H_2O$, 30 µl of 10% APS, 10 µl of TEMED). Running parameters were 180 V, 400 mA, and 60 W for 1.5 h.

In-Gel Fluorescence Detection

After SDS-PAGE, labeled proteins were visualized at 50-µm resolution in gels using a Typhoon 9210 gel scanner (Amersham Biosciences) with 580-nm bandpass filter for TAMRA. All gel images were analyzed using ImageJ software (National Institutes of Health). The background signal of the gel images was subtracted, and the brightness and contrast were adjusted to optimize the signal-to-noise ratio (all operations were performed over the entire gel uniformly).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A conjugate selected from:

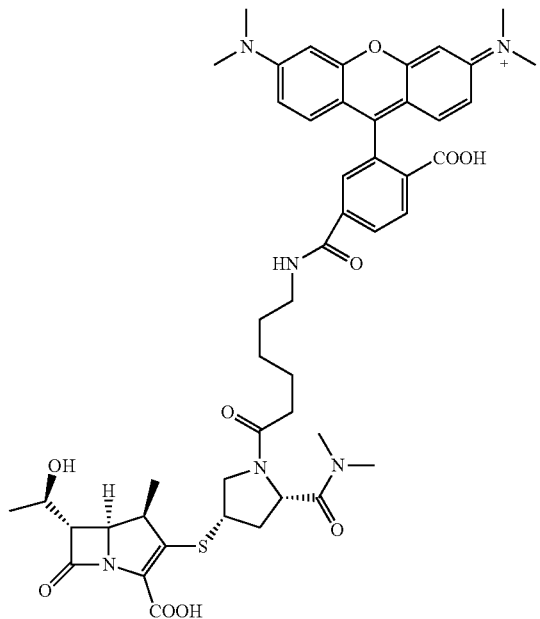

-continued
and
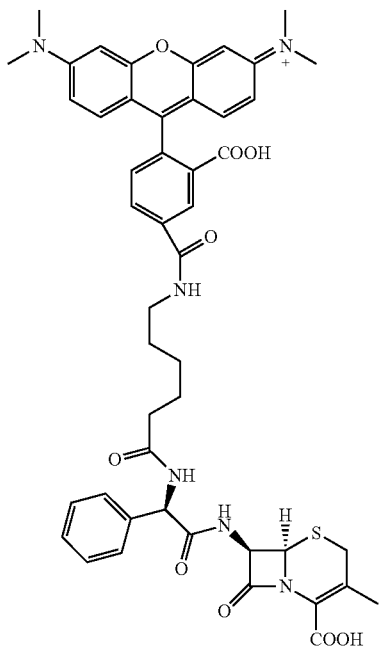
or a salt thereof.
2. The conjugate or salt of claim 1, which is:
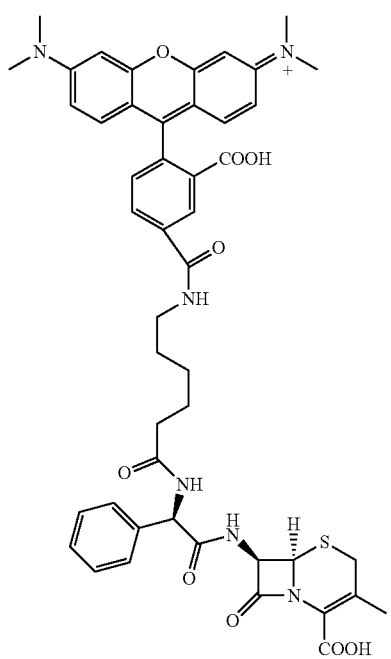
or a salt thereof.
* * * * *